US00PP18821P2

(12) United States Plant Patent
Repp

(10) Patent No.: US PP18,821 P2
(45) Date of Patent: May 20, 2008

(54) ***LANTANA* PLANT NAMED 'TROPICAL FRUIT'**

(50) Latin Name: *Lantana camara*
Varietal Denomination: Tropical Fruit

(76) Inventor: Ralph J. Repp, 160 Gator Dr., Waynesville, NC (US) 28785

( * ) Notice: Subject to any disclaimer, the term of this patent is extended or adjusted under 35 U.S.C. 154(b) by 0 days.

(21) Appl. No.: 11/518,581

(22) Filed: Sep. 8, 2006

(51) Int. Cl.
*A01H 5/00* (2006.01)

(52) U.S. Cl. ..... Plt./227
(58) Field of Classification Search ..... Plt./227
See application file for complete search history.

(56) References Cited

PUBLICATIONS

BioFlora—Nature Knows Best[retrieved on Aug. 14, 2007]. Retrieved from the Internet <http://www.bioflora.com/>5 pages.*

UPOV–ROM GTITM, Plant Variety Database, 2007/01, GTI Jouve Retrieval Software, Citation for Lantana 'Tropical Fruit', one page.*

* cited by examiner

*Primary Examiner*—Kent Bell
*Assistant Examiner*—June Hwu
(74) *Attorney, Agent, or Firm*—C. A. Whealy

(57) ABSTRACT

A new and distinct cultivar of *Lantana* plant named 'Tropical Fruit', characterized by its mounding and outwardly spreading growth habit; freely branching plant habit; yellow-green and dark green variegated foliage; freely flowering habit; and yellow-colored flowers that are held above and beyond the foliage.

1 Drawing Sheet

Botanical designation: *Lantana camara*. Cultivar denomination: 'Tropical fruit'.

BACKGROUND OF THE INVENTION

The present invention relates to a new and distinct cultivar of *Lantana,* botanically known as *Lantana camara,* and hereinafter referred to by the name 'Tropical Fruit'.

The new *Lantana* is a product of a planned breeding program conducted by the Inventor in Waynesville, N.C. The objective of the breeding program is to create new freely-flowering *Lantana* cultivars with attractive flower coloration.

The new *Lantana* is a naturally-occurring whole plant mutation of an unnamed proprietary seedling selection, not patented. The new *Lantana* was discovered and selected by the Inventor from within a population of plants of the seedling selection in a controlled environment in Waynesville, N.C. in June, 2002.

Asexual reproduction of the new *Lantana* by terminal cuttings in a controlled environment in Waynesville, N.C. since September, 2002, has shown that the unique features of this new *Lantana* are stable and reproduced true to type in successive generations.

SUMMARY OF THE INVENTION

The cultivar Tropical Fruit has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Tropical Fruit'. These characteristics in combination distinguish 'Tropical Fruit' as a new and distinct cultivar of *Lantana:*

1. Mounding and outwardly spreading growth habit.

2. Freely branching plant habit;
3. Yellow-green and dark green variegated foliage.
4. Freely flowering habit.
5. Yellow-colored flowers that are held above and beyond the foliage.

Plants of the new *Lantana* can be compared to plants of the parent selection. Plants of the new *Lantana* differ from plants of the parent selection primarily in foliage color as plants of the parent selection have light green-colored foliage. In addition, plants of the new *Lantana* and the parent selection differ in flower color as plants of the parent selection have light yellow-colored flowers.

Plants of the new *Lantana* can be compared to plants of the *Lantana* cultivar Lemon Drop, not patented. Plants of the new *Lantana* differ from plants of the cultivar Lemon Drop primarily in foliage color as plants of the cultivar Lemon Drop have light green-colored foliage. In addition, plants of the new *Lantana* and the cultivar Lemon Drop differ in flower color as plants of the cultivar Lemon Drop have light yellow-colored flowers.

BRIEF DESCRIPTION OF THE PHOTOGRAPHS

The accompanying colored photographs illustrate the overall appearance of the new *Lantana,* showing the colors as true as it is reasonably possible to obtain in colored reproductions of this type. Colors in the photographs may differ slightly from the color values cited in the detailed botanical description which accurately describe the colors of the new *Lantana.*

The photograph at the bottom of the sheet comprises a side perspective view of a typical flowering plant of 'Tropical Fruit' grown in a container.

The photograph at the top of the sheet is a close-up view of typical inflorescences and leaves of 'Tropical Fruit'.

DETAILED BOTANICAL DESCRIPTION

The aforementioned photographs and following observations and measurements describe plants grown in Bonsall, Calif., under commercial practice during the summer in an outdoor nursery with day temperatures ranging from 18° C. to 35° C. and night temperatures ranging from 10° C. to 21° C. Plants were grown with one rooted cutting per 10-cm container for about seven weeks. In the following description, color references are made to The Royal Horticultural Society Colour Chart, 1995 Edition, except where general terms of ordinary dictionary significance are used.

Botanical Classification: *Lantana camara* cultivar Tropical Fruit.

Parentage: Naturally-occurring whole plant mutation of an unnamed proprietary seedling selection, not patented.

Propagation:

*Type.*—By terminal cuttings.

*Time to initiate roots, summer.*—About 10 days.

*Time to initiate roots, winter.*—About 14 days.

*Time to produce a rooted young plant, summer.*—About three weeks.

*Time to produce a rooted young plant, winter.*—About four weeks.

*Root description.*—Fine, fibrous; white to brown in color.

*Rooting habit.*—Moderate branching.

Plant description:

*Plant habit.*—Initially upright, the outwardly spreading and mounding. Freely branching habit; about six primary lateral branches per plant each with numerous secondary branches; pinching enhances lateral branch development; dense and bushy plant habit. Vigorous growth habit.

*Plant height.*—About 22 cm.

*Plant diameter.*—About 64 cm.

Lateral branch description:

*Length.*—About 34 cm.

*Diameter.*—About 3 mm.

*Internode length.*—About 3.8 cm.

*Strength.*—Flexible but strong.

*Texture.*—Hirsute to echinate.

*Color.*—146A.

Foliage description:

*Arrangement.*—Opposite, simple.

*Length.*—About 4.5 cm.

*Width.*—About 2.8 cm.

*Shape.*—Elliptical.

*Apex.*—Acute.

*Base.*—Obtuse.

*Margin.*—Serrulate.

*Texture, upper and lower surfaces.*—Coarse, rough; minute pubescence.

*Venation pattern.*—Pinnate; arcuate.

*Color.*—Developing foliage, upper surface: 146A with random and irregular mottling, 146C to 146D. Developing foliage, lower surface: 146B. Fully expanded foliage, upper surface: 147C with random and irregular mottling, 147A to 147B and 146D; venation, 147C. Fully expanded foliage, lower surface: 147B with random and irregular mottling, 146D; venation, 147D.

*Petiole.*—Length: About 8 mm. Diameter: About 1.5 mm. Texture, upper and lower surfaces: Rough, scattered pubescence. Color, upper and lower surfaces: 146C.

Flower description:

*Flower arrangement and habit.*—Solitary tubular flowers arranged in axially umbels; flowers face mostly upward or outward. Freely flowering habit with potentially two inflorescences developing per node, each umbel with about 30 flowers.

*Natural flowering season.*—Spring until frost in the autumn; flowering continuous during this period.

*Flower longevity on the plant.*—About four to five days. Flowers not persistent.

*Fragrance.*—Slightly fruity.

*Inflorescence height.*—About 1.7 cm.

*Inflorescence diameter.*—About 3.8 cm.

*Flowers.*—Appearance: Flared trumpet, corolla fused, four-parted. Diameter: About 1 cm. Depth (height): About 1.5 cm.

*Flower buds.*—Tube length: About 1.3 cm. Tube diameter. About 2 mm. Length: about 1.3 cm. Diameter: About 4 mm. Shape: Elongate, oblong. Color: 11C.

*Corolla.*—Arrangement: Single whorl or four fused petals. Petal lobe length: About 4 mm to 5 mm. Petal lobe width: About 6 mm. Petal lobe shape: Roughly ovoid. Petal lobe apex: Rounded. Petal margin: Entire, slightly sinuate. Petal texture, upper and lower surfaces: Smooth, glabrous. Color: When opening and fully opened, upper surface: 12C; towards the margins, 11C; towards the throat, 14A. Width development, margins blushed with 49C. When opening and fully opened, lower surface: 11D. Throat and tube: Close to 11D.

*Calyx.*—Arrangement: One single calyx tube per flower. Calyx length: About 2 mm. Calyx width: About 1.5 mm. Apex: Rounded. Texture, upper and lower surfaces: Smooth, glabrous. Color, upper and lower surfaces: 146D.

*Peduncles.*—Length: About 5 cm to 5.5 cm. Diameter: About 1 mm. Strength: Flexible, but strong. Texture: Minute pubescence. Color: 146B.

*Pedicels.*—Length: Less than 1 mm. Diameter: Less than 1 mm. Color: Close to 146B.

*Reproductive organs.*—Stamens: Quantity/arrangement: Four per flower, adnate to floral tube: Anther shape: Oval. Anther length: Less than 1 mm. Anther color: 11A. Pollen amount: Scarce. Pollen color: 11A. Pistils: Quantity: One per flower. Pistil length: About 4 mm. Stigma shape: Bi-lobed, rounded. Stigma color: 145C. Style length: About 2 mm. Style color: 145D. Ovary color: 145A. Fruits/seed: Fruit and seed development have not been observed.

Temperature tolerance: Plants of the new *Lantana* have been observed to tolerate temperatures from about 2° C. to about 32° C.

Pathogen/pest resistance: Plants of the new *Lantana* have not been observed to be resistant to pests and pathogens common to *Lantanas*.

It is claimed:

1. A new and distinct *Lantana* plant named 'Tropical Fruit' as illustrated and described.

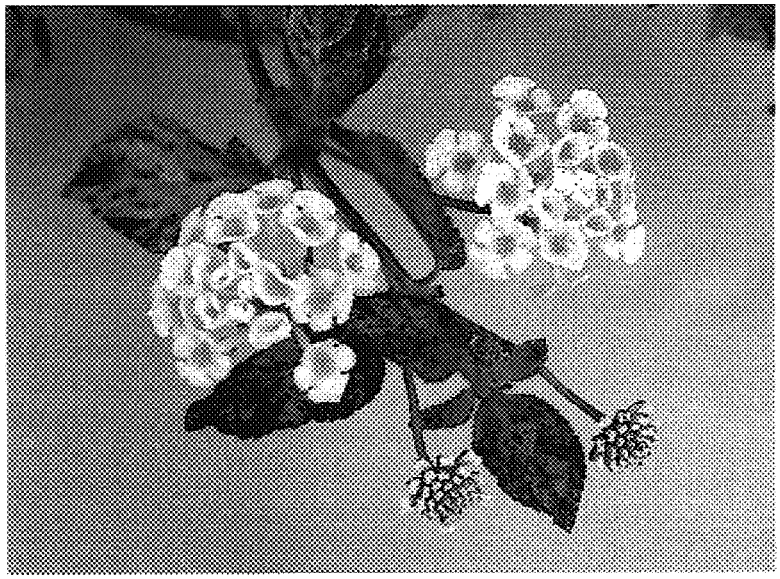
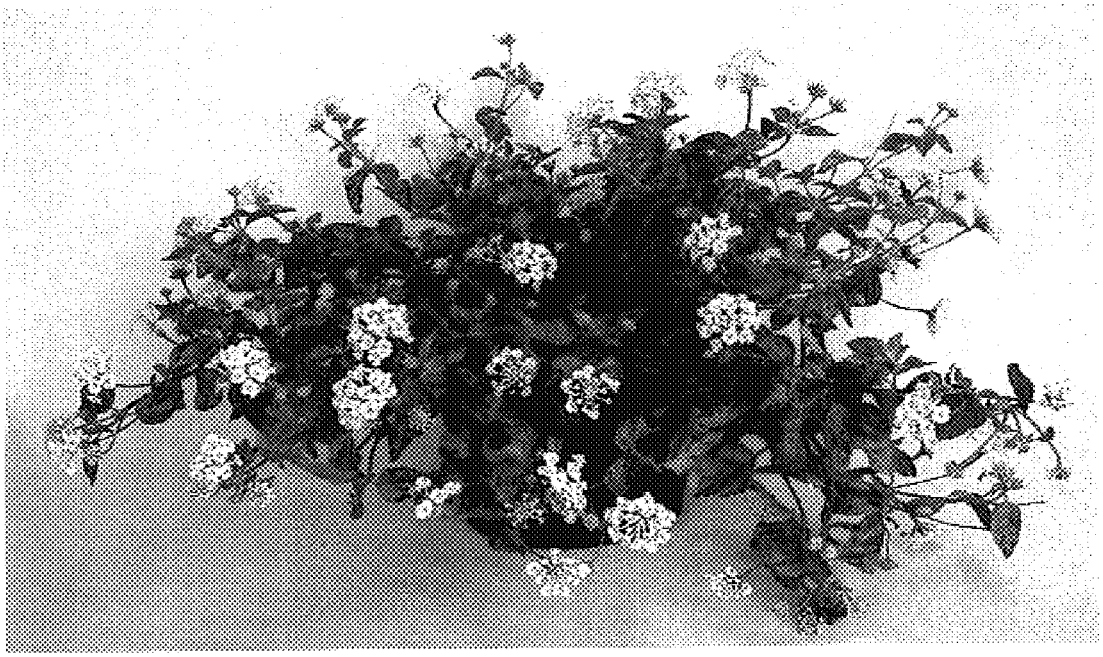

* * * * *